US00PP14407P39

(12) United States Plant Patent
Pieters

(10) Patent No.: US PP14,407 P3
(45) Date of Patent: Dec. 23, 2003

(54) CHRYSANTHEMUM PLANT NAMED 'GEDI TWO RAN'

(50) Latin Name: *Chrysanthemum morifolium*
Varietal Denomination: Gedi Two Ran

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,803

(22) Filed: May 1, 2002

(65) Prior Publication Data

US 2003/0208819 P1 Nov. 6, 2003

(51) Int. Cl.[7] ..... A01H 5/00

(52) U.S. Cl. ..... Plt./293

(58) Field of Search ..... Plt./293, 287, 292

(56) References Cited

U.S. PATENT DOCUMENTS

PP10,213 P 1/1998 Wain ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 50 days of short day length, free branching habit, red ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Ran'.

BACKGROUND OF THE INVENTION

The new cultivar is a product of hybridization of a female parent variety, 'Gedi Two Cam' (U.S. patent application Ser. No. 10/138,116) and a male parent variety 'Medonia Red' (undistributed in the United States). The new cultivar was discovered and selected by the inventor in October 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Ran' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Ran.' These characteristics in combination distinguish 'Gedi Two Ran' as a new and distinct Chrysanthemum cultivar:

1. Decorative-type inflorescence,
2. Consistent flowering response to short days, blooming consistently after 50 days of short day length,
3. Free branching habit,
4. Red ray florets,
5. Very uniform round growth habit, and
6. Large quantity of blooms per flowering branch.

Plants of the new cultivar are similar to plants of the female parent variety, 'Gedi Two Cam' in most horticultural characteristics, however plants of the new cultivar have more ray florets per inflorescence and inflorescences with a smaller diameter than the female parent variety. Plants of the new cultivar also bloom naturally two weeks earlier than plants of the female parent variety.

Plants of the new cultivar are similar to plants of the male parent variety, 'Medonia Red,' however the new cultivar has ray florets which are a lighter red color than plants of the male parent variety. Plants of the new cultivar also bloom naturally three weeks earlier than plants of the male parent variety, and plants of the new cultivar have fewer inflorescences per flowering branch than plants of the 'Medonia Red' variety.

In comparison to the commercially available variety 'Jenny Wren' (U.S. Plant Pat. No. 10,213), 'Gedi Two Ran' has ray florets of a different color, fewer ray florets per inflorescence, leaves that are more than twice as large, and more blooms per flowering branch.

BRIEF DESCRIPTION OF THE PHOTOGRAPH

The photograph shows a close-up of the inflorescence and foliage of 'Gedi Two Ran', which was grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 84 days from a rooted cutting. The growing temperature ranged from 55° to 68° F. at night to 60° to 75° F. during the day.

Measurements and numerical values represent averages of typical flowering types.

Botanical classification: *Chrysanthemum morifolium* cultivar 'Gedi Two Ran'.
Commercial classification: Garden-type Chrysanthemum.
Parentage: Hybridization of a female parent variety, 'Gedi Two Cam' (U.S. patent application Ser. No. 10/138,116), and a male parent variety 'Medonia Red' (undistributed in the United States).

PROPAGATION

Time to rooting: 7 to 14 days at approximately 21° C.
Root description: Fine, fibrous.

PLANT

Growth habit: Mounding herbaceous perennial.
Height: Approximately 20 cm.
Spread: Approximately 22 cm.
Growth rate: Moderate.
Branching characteristics: Free Branching.
Length of lateral branches: Approximately 20.5 cm.
Number of leaves per lateral branch: Approximately 13.

FOLIAGE

Leaf:
- *Arrangement.*—Alternate.
- *Average length.*—Approximately 6.5 cm.
- *Average width.*—Approximately 5.1 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137B. Young foliage under side: Near 138B. Mature foliage upper side: Near 137B. Mature foliage under side: Near 138B. Venation upper side: Near 145A. Venation under side: Near 138C.
- *Venation type.*—Palmately net.

Petiole:
- *Average length.*—Approximately 2.8 cm.
- *Color.*—Near 137B.
- *Diameter.*—Approximately 0.3 cm.

BLOOM

Inflorescence:
- *Flowering habit.*—Induced by darkness period greater than 13.5 hours, approximately 50 days of appropriate day length required to induce and develop blooms.
- *Inflorescence form.*—Decorative.
- *Natural flowering season.*—Approximately the first two weeks of September.
- *Number of inflorescences per lateral branch.*—Approximately 14.
- *Inforescence diameter.*—Approximately 4 cm.
- *Inflorescence depth.*—Approximately 1.5 cm.
- *Inflorescence longevity on plant.*—Approximately 15 days.
- *Persistence.*—Persistent.

Ray florets:
- *Appearance.*—Matte.
- *Texture.*—Smooth.
- *Average number per flower.*—153.
- *Shape.*—Oblong.
- *Aspect.*—Flat.
- *Margin.*—Entire.
- *Apex.*—Retuse.
- *Length.*—Approximately 2.2 cm.
- *Width.*—Approximately 0.8 cm.
- *Color.*—Upper surface at first opening: Near 185A. Upper surface at maturity: Near 48B. Upper surface at fading: Near 179A. Under surface at first opening: Near 182B. Under surface at maturity: Near 181D. Under surface at fading: Near 179C.

Disc florets:
- *Appearance.*—Shiny.
- *Texture.*—Smooth.
- *Average number per flower.*—Approximately 3.
- *Shape.*—Cylindric.
- *Apex.*—Obtuse.
- *Average length.*—Approximately 0.3 cm.
- *Average width.*—Approximately 0.1 cm.
- *Color.*—At first opening: Near 154B. At maturity: Near 2B. At fading: Near 6A.

Peduncle:
- *Length.*—At terminal end (shortest): Approximately 2.6 cm. At lateral end (longest): Approximately 9 cm.
- *Angle to stem.*—Acute.
- *Strength.*—Moderate.
- *Color.*—Near 138B.
- *Habit.*—Upright.
- *Diameter.*—Approximately 0.2 cm.
- *Surface texture.*—Lightly pubescent.

Inflorescence bud:
- *Length.*—Approximately 0.7 cm.
- *Diameter.*—Approximately 0.7 cm.
- *Form.*—Globular.
- *Color* (*as ray florets first emerge*).—Near 187C.

Involucral bracts (phyllaries):
- *Appearance.*—Matte.
- *Texture.*—Lightly pubescent.
- *Number.*—Approximately 25.
- *Shape.*—Oblanceolate.
- *Margin.*—Entire.
- *Apex. Acute.*
- *Length.*—Approximately 0.7 cm.
- *Width.*—Approximately 0.4 cm.
- *Color.*—Upper side: Near 143A. Under side: Near 138A.

REPRODUCTIVE ORGANS

Ray florets:
- *Number of pistils per flower.*—1.
- *Stigma shape.*—2 branched.
- *Stigma color.*—Near 1A.
- *Style color.*—Near 1C.
- *Style length.*—Approximately 0.4 cm.
- *Stamens.*—Absent.

Disc florets:
- *Number of pistils per flower.*—11.
- *Stigma shape.*—Two-branched.
- *Stigma color.*—Near 2A.
- *Style length.*—Approximately 0.4 cm.
- *Style color.*—Near 154C.
- *Number of stamens per flowers.*—5.
- *Anther shape.*—Tubular.
- *Anther color.*—Near 15A.
- *Pollen.*—No pollen detected.

OTHER CHARACTERISTICS

Seed production: Commercially, this plant is not used or observed, in a stage wherein seeds would be produced. Therefore, seed production has not been observed.

Disease Resistance: Neither resistance nor susceptibility to diseases and pests has been observed in this cultivar.

Heat and cold Resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Ran' as herein illustrated and described.

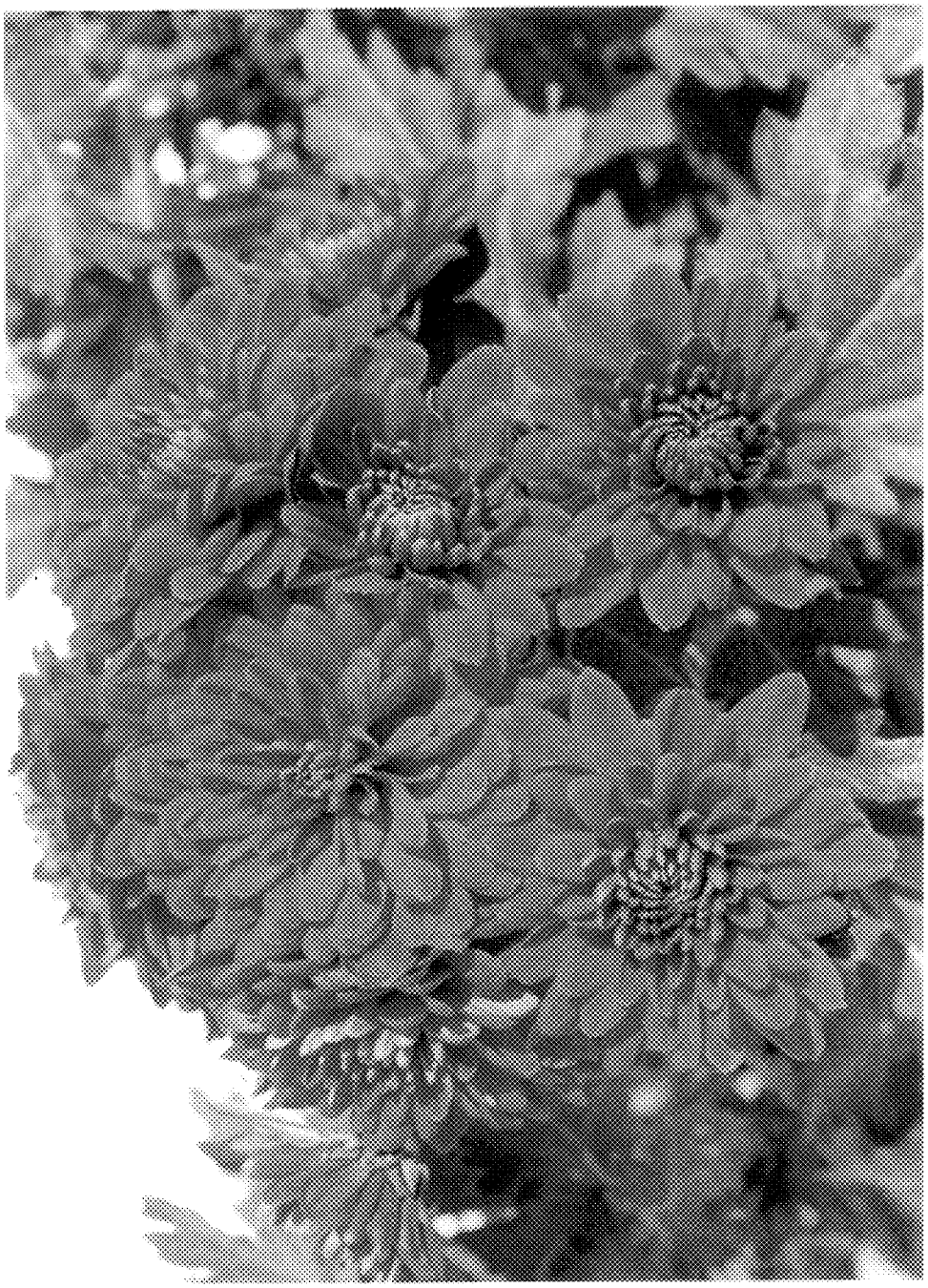

* * * * *